(12) United States Patent
Magnusson et al.

(10) Patent No.: US 6,610,898 B1
(45) Date of Patent: Aug. 26, 2003

(54) FLUID ACQUISITION/TRANSFER LAYER IN AN ABSORBENT ARTICLE

(75) Inventors: Ing-Britt Magnusson, Mölnlycke (SE); Christina Steger, Mölndal (SE)

(73) Assignee: SC Hygiene Products AB, Gothenburg (SE)

( * ) Notice: Subject to any disclaimer, the term of this patent is extended or adjusted under 35 U.S.C. 154(b) by 0 days.

(21) Appl. No.: 09/445,484

(22) PCT Filed: Jun. 23, 1998

(86) PCT No.: PCT/SE98/01223

§ 371 (c)(1),
(2), (4) Date: Dec. 7, 1999

(87) PCT Pub. No.: WO99/00098

PCT Pub. Date: Jan. 7, 1999

(30) Foreign Application Priority Data

Jun. 26, 1997 (SE) ................................... 9702461

(51) Int. Cl.[7] .......................... A61F 13/15; A61F 13/20
(52) U.S. Cl. ....................... 604/366; 604/365; 604/367
(58) Field of Search ............................. 604/366, 365, 604/367, 370

(56) References Cited

U.S. PATENT DOCUMENTS

| | | | | |
|---|---|---|---|---|
| 3,371,667 A | | 3/1968 | Morse ....................... 128/290 |
| 4,652,484 A | | 3/1987 | Shiba et al. ................ 428/286 |
| 4,883,707 A | | 11/1989 | Newkirk .................... 428/219 |
| 5,486,166 A | * | 1/1996 | Bishop et al. .............. 604/366 |
| 5,522,810 A | * | 6/1996 | Allen, Jr. et al. .......... 604/366 |
| 5,556,392 A | | 9/1996 | Koczab ..................... 604/378 |
| 5,968,855 A | * | 10/1999 | Perdelwitz, Jr. et al. .... 442/341 |
| 5,989,688 A | * | 11/1999 | Barge et al. ............... 428/198 |

FOREIGN PATENT DOCUMENTS

| | | |
|---|---|---|
| DE | 195 17 348 | 8/1996 |
| EP | 0 306 262 | 3/1989 |
| EP | 0 312 118 | 4/1989 |
| EP | 0 729 735 | 3/1995 |
| EP | 0 747 521 | 6/1995 |
| EP | 0 665 315 | 8/1995 |
| GB | 2 214 201 | 8/1989 |
| JP | 1-260051 | 10/1989 |
| JP | 1-298206 | 12/1989 |
| WO | 98/29071 | 7/1989 |
| WO | 90/14814 | 12/1990 |

* cited by examiner

*Primary Examiner*—Weilun Lo
*Assistant Examiner*—Jacqueline Stephens
(74) *Attorney, Agent, or Firm*—Burns, Doane, Swecker & Mathis, L.L.P.

(57) ABSTRACT

A fluid liquid acquisition/transfer layer in an absorbent article, such as a diaper, pant diaper, incontinence guard, sanitary napkin, panty liner or the like. The fluid acquisition/transfer layer includes a mixture of heat-shrunk, spiralized, thermoplastic multicomponent, preferably bicomponent, functional fibers of 3.4 dtex or more. The components of the functional fibers each have different shrinkage properties and are located in a side-by-side relationship for creating the spiralized shape of the functional fibers. The fluid acquisition/transfer layer also includes bonding fibers that bond to each other through heat treatment while the functional fibers do not bond to each other during heat treatment.

20 Claims, 5 Drawing Sheets

FLUID ACQUISITION/TRANSFER LAYER IN AN ABSORBENT ARTICLE

TECHNICAL FIELD

The present invention refers to a fluid acquistion/transfer layer in an absorbent article, such as a diaper, pant diaper, incontinence guard, sanitary napkin, panty liner or the like.

BACKGROUND OF THE INVENTION

An absorbent article usually comprises several layers, a fluid pervious topsheet intended to be worn in contact with the wearer, a fluid acquisition/transport layer for quickly acquiring body fluids, an absorbent core for absorbing and storing the body fluids and a liquid impervious backsheet. The fluid acquisition/transport layer has an open porous structure and it shall be able to quickly receive and temporarily store a certain amount of fluid and transfer it further to the underlying absorbent core. The fluid acquisition/ transport layer usually is a so called high loft material produced by carding and thru-air bonding or needling a synthetic fibers, such as polyester, polypropylene or mixtures thereof. It could also comprise a porous foam material. Examples of absorbent articles comprising a porous fluid acquisition/transport layer are found in U.S. Pat. No. 3,371, 667, EP-A-0,312,118, EP-A-474,777 and U.S. Pat No. 5,556,392.

The use of heat-shrunk, spiralized, thermoplastic bicomponent fibers of a side-by-side type in a topsheet material is disclosed in the intermediate document PCT/SE97/02074. The fibers should be very thin, 1.5–3.3 dtex, in order to be soft against the skin of the wearer since they are used in the topsheet of an absorbent article. The topsheet may further comprise heat-activateable bonding fibers which have been bonded together by heat treatment. Such spiralized bicomponent fibers of side-by-side type provides an open and lofty structure which is very resilient also after compression. Heat shrinkage and spiralization of the fibers can be provided by the supplier or in-line during manufacture of the transfer layer.

EP-A-0 729 735 discloses a topsheet in an absorbent article comprising eccentric bicomponent fibers which crimp when heated. They have a length of 3–12 mm and are dry formed on top of the absorbent core. Heat treatment then is performed in order to crimp the eccentric bicomponent fibers and to bind them together. Such bonding of the crimped fibers will seriously detoriate their resiliency.

EP-A-0 306 262 and GB-A-2 214 201 further disclose absorbent structures in e g diapers and sanitary napkins, which comprise crimped fibers in order to give resiliency to the structure and resistance to folding during use of the absorbent article.

SUMMARY OF THE INVENTION

The object of the present invention is to provide a fluid acquistion/transfer layer having an open and lofty structure which is very resilient after compression and which layer is effective in receiving and temporarily storing body liquids and transfer is further to the underlying absorbent core. This has been accomplished by the fact that said fluid acquisitionl/transfer layer comprises a mixture of heat-shrunk, spiralized, thermoplastic multicomponent, preferably bicomponent, functional fibers of 3.4 dtex or more, in which the components of said fibers have mutually different shrinkage properties and are located in a side-by-side relationship, and thermoplastic bonding fibers which have been bonded together by heat treatment, while said functional fibers are substantially unbonded by said heat treatment.

Further features of the fluid acquistion/transfer layer according to the present invention are stated in the claims and in the detailed description below.

The invention also refers to an absorbent article such as a diaper, pant diaper, incontinence guard, sanitary napkin panty liner or the like, comprising a liquid pervious topsheet, a liquid impervious backsheet, an absorbent core and a fluid acquisition/transfer layer arranged between the topsheet and the absorbent core, wherein said fluid acquisition/transfer layer is of the kind stated above.

DESCRIPTION OF THE DRAWINGS

The invention will now be further described with reference to the accompanying drawings, wherein.

DESCRIPTION OF EMBODIMENTS

Figure 1:
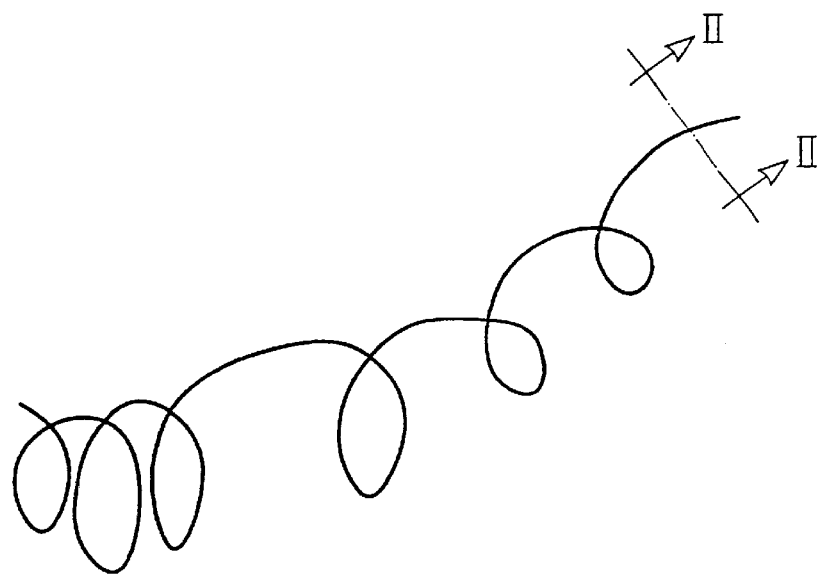
FIG. 1 is a schematic view of a spiralized bicomponent fiber.

The fluid acquisition/transfer layer according to the invention comprises a mixture of heat-shrunk spiralized, thermoplastic multicomponent functional fibers of side-by-side type, preferably bicomponent fibers, and thermoplastic bonding fibers. A spiralized fiber is schematically shown in FIG. 1.

Figure 2A:
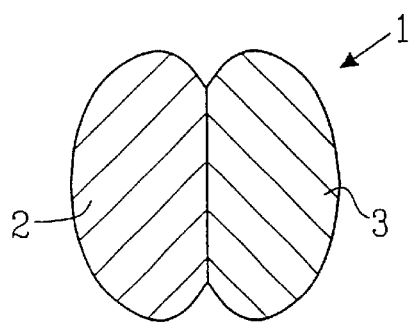
FIGS. 2a–d show enlarged cross sections according to the line II—II in FIG. 1 of four examples of bicomponent fibers of side-by-side type.
Figure 2B:
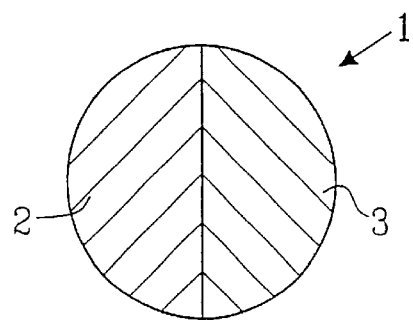
Figure 2C:
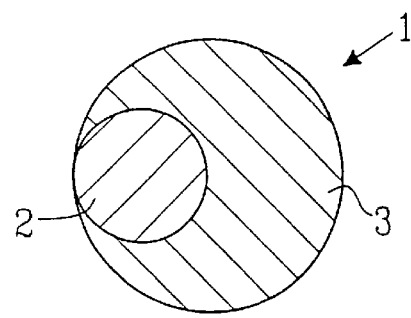

In the following the invention will be described referring to bicomponent fibers, although it is understood that the fiber can comprise three or more components. Different types of side-by-side bicomponent fibers 1 can be used. In FIG. 2a is shown an example where the two components 2,3 both have an elliptic shape and are interconnected along a part of the fibre surface. A second type is shown in FIG. 2b, where the cross-section of the fiber is substantially circular and each component 2,3 has a semicircular shape. A third type is shown in FIG. 2c, where the bicomponent fiber is of an eccentric type. The first component 2 is a core eccentrically located in the surrounding casing formed by the other component 3. The core formed by the first component 2 is located within the casing formed by the second component 2 in such a way that the second component 3 does not cover the part of the surface of the first component located at the periphery of the fiber. Thus the first component will have one free surface portion.

Figure 2D:
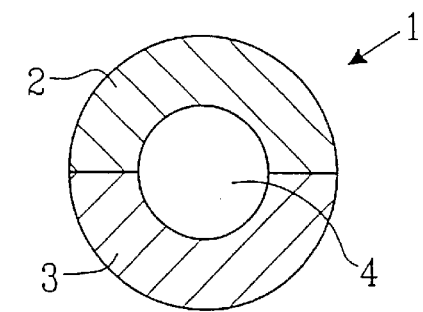

In FIG. 2d is shown an embodiment of a bicomponent fiber having a hollow structure. Each component 2,3 has a semicircular shape and are interconnected so as to form a hollow space 4 in the centre of the fiber. The shape and size of the hollow space 4 can vary and is not limited to what is shown in the drawings.

It is important to choose components 2,3 having mutually different shrinkage properties. When heat treating such a fiber the two components will shrink differently, so that one side of the fiber will be shorter than the other, at which the fiber will twist and shrink into a spiral shape, as is shown in FIG. 1. The polymers used for the different components can be of any kind, such as polyolefines, polyester, copolyester, polyamide, copolyamide, polyacrylates etc.

The thickness of the functional bicomponent fiber used in the fluid acquisition/transfer layer according to the invention is between 3.4 and 50 dtex, preferably between 3,4 and 15 dtex. Their length can vary depending on whether used as a carded web, in which their length should be between 20 and 80 mm, preferably between 40 and 60 mm, or as an airlaid or wetlaid web in which fibers shorter than 20 mm are preferably used.

The functional fibers 1 may be hydrophilized in order to give the fluid acquisition/transfer layer more hydrophilic properties.

The fluid acquisition/transfer layer further comprises thermoplastic bonding fibers 5, which may be of a one-component or bi- or multicomponent type. The bonding fibers 5 should have a lower melting point than the functional fibers, so that the fiber mixture can be heated to a temperature between the melting points of the bonding fibers and the functional fibers respectively, in order to bind the material. In this way only the bonding fibers will melt, while the functional fibers are substantially uneffected by the heat treatment and will maintain their resiliency resulting in a more open and resilient material.

Examples of thermoplastic bonding fibers are polyethylene, polypropylene, copolyester/polyester.

The content of functional and bonding fibers can vary, however the content of functional fibers should be at least 40 and preferably at least 50% by weight, and the content of bonding fibers should be at least 10% by weight. Other fibers can also be incorporated in the fluid acquisition/transfer layer according to the invention. Examples of such fibers are cellulosic fibers, preferably crosslinked cellulosic fibers.

The fluid acquisition/transfer layer could also be in the form of a laminate in which the fiber composition in the different layers of the laminate could vary in order to give the individual layers different properties. The upper layer could e g contain a high amount of spiralized functional fibers in order to rapidly acquire discharged body fluid and the lower layer(s) facing the absorbent core could contain a smaller amount or even no at all of the spiralized functional fibers and instead contain other types of hydrophilic fibers, e g crosslinked cellulosic fibers. Both layers should however contain bonding fibers and be thermally bonded. In case of a laminate the calculation of fiber content of e g the spiralized functional fibers should be made for the individual layers of the laminate.

The fluid acquisition/transfer layer may further be connected a carrier layer, e g a nonwoven, an airlaid tissue or the like.

The bonding technique preferably used for thermally bonding the material layer is so called thru-air bonding, in which an open structure of the material layer is maintained.

Heat shrinkage and spiralization of the functional bicomponent fibers can either be provided by the supplier or in-line during manufacture of the absorbent article. In the latter case heat shrinkage and spiralization of the functional bicomponent fibers and bonding of the bonding fibers can be provided at the same time.

Figure 3:
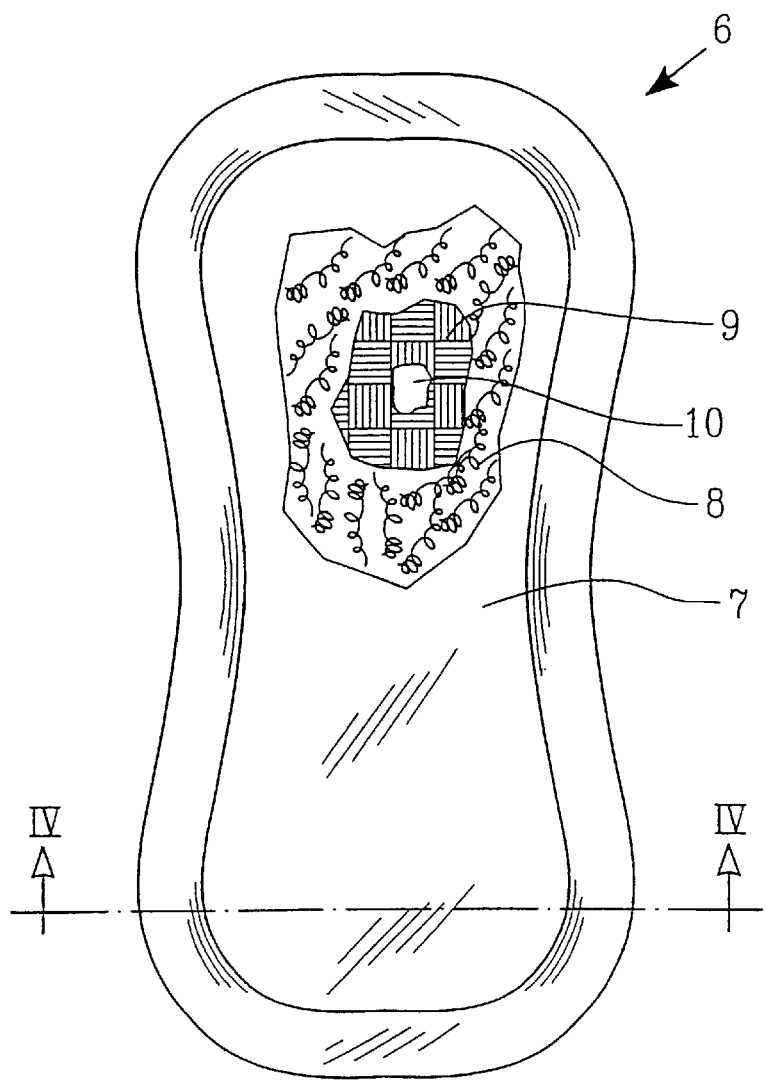
FIG. 3 is a plan view of an incontinence guard.
Figure 4:
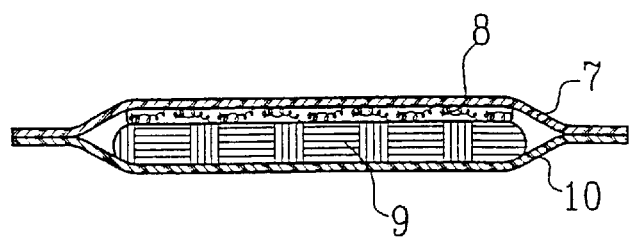
FIG. 4 is a section according to the line IV—IV in FIG. 3.
Figure 5:
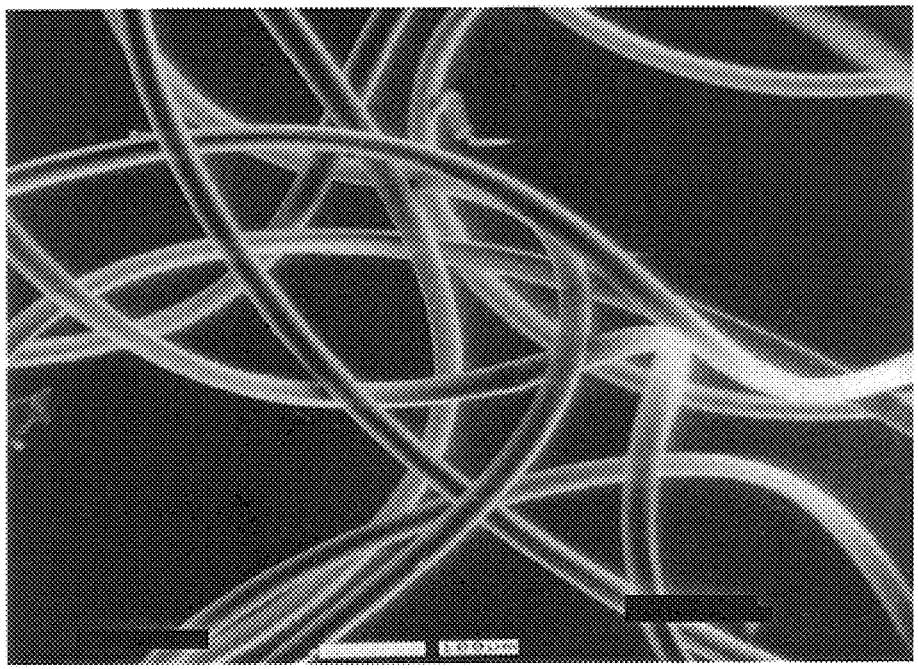
FIG. 5 shows a photo in 100 times magnification taken with a scanning electron microscope of an example of spiralized hollow functional fibers usable in the fluid acquisition/transfer layer according to the invention.
Figure 6:
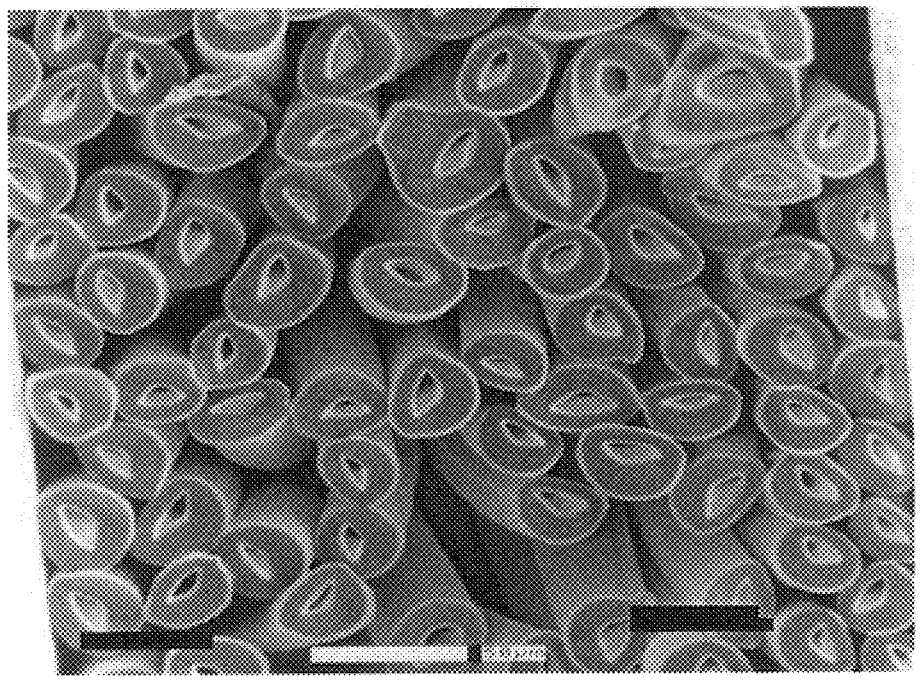
FIG. 6 shows a photo in 300 times magnification of a cross section through the functional fibers in FIG. 5.
Figure 7:
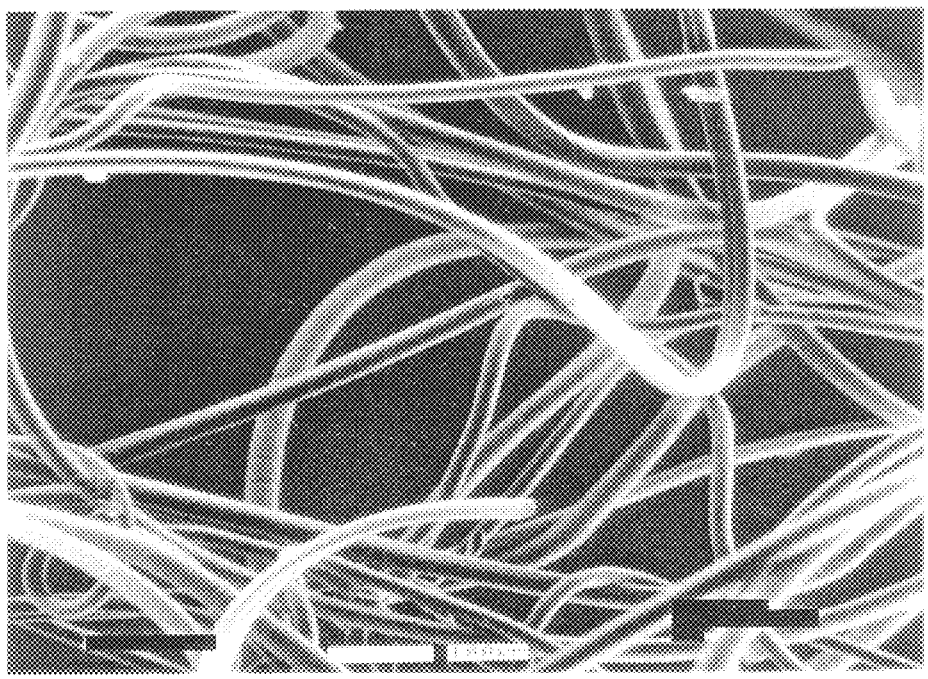
FIG. 7 shows a photo in 100 times magnification taken with a scanning electron microscope of an example of the material according the invention.
Figure 8:
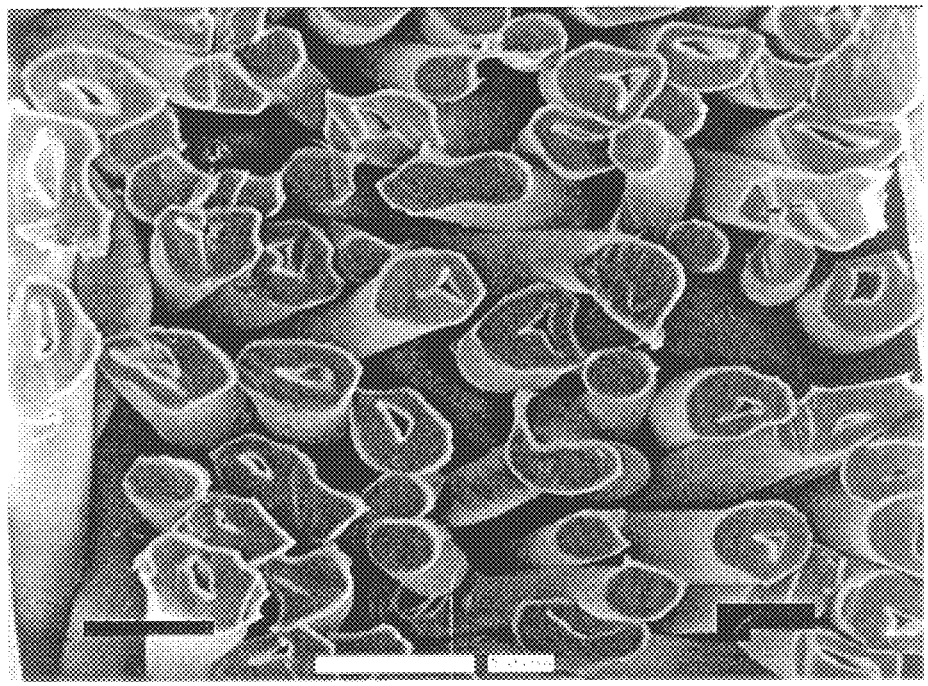
FIG. 8 shows a photo in 300 times magnification of a cross section through the fibers of the material in FIG. 7.
Figure 9:
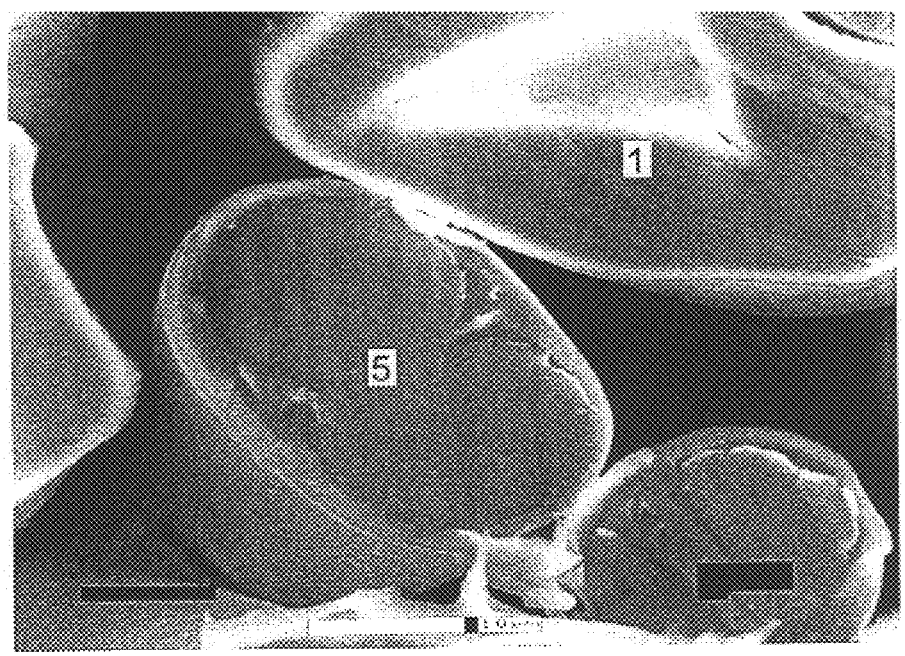
FIG. 9 shows a photo in 1500 times magnification of a cross section through the bonding fibers used in the material in FIGS. 7 and 8.
Figure 10:
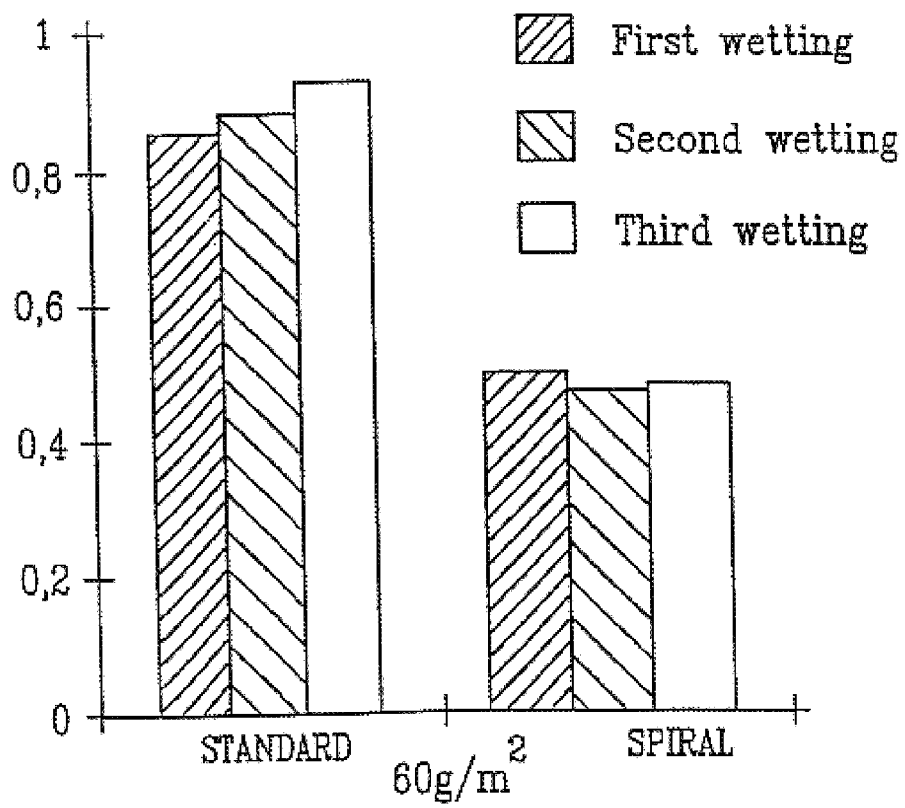
FIG. 10 is a bar chart showing the results of comparative tests of the penetration time through a known fluid acquisition/transfer layer and a layer according to the present invention.

The invention also refers to an absorbent article such as a diaper, pant diaper, incontinence guard, sanitary napkin, panty liner or the like containing a fluid acquisition/transfer layer as described above. An example of an absorbent article in the form of an incontinence guard 6 is disclosed in FIGS. 3 and 4 of the drawings. The incontinence guard comprises a liquid pervious topsheet 7 intended to be facing the wearer during use of the article, a fluid acquisition/transfer layer 8 adapted to rapidly acquire and temporarily store body liquids and transfer it to an underlying absorbent core 9, and a liquid impervious backsheet 10.

The liquid pervious topsheet 7 can be a nonwoven material, such as a spunlaid material of synthetic filaments or a thermobonded carded fibrous web. It could also be a perforated plastic film. The liquid impervious backsheet 10 can be a plastic film, a nonwoven material coated with a liquid impervious material or a hydrophobic nonwoven which resists penetration by liquids.

The topsheet 7 and backsheet 10 has a larger extension in the x-y-plane than the fluid acquisition/transfer layer 8 and the absorbent core 9 and extend outside the edges thereof. The topsheet 7 and backsheet 10 are interconnected along their projecting edges, e g by gluing or welding by heat or ultrasonics.

The absorbent core 9 can be of any kind. Examples of commonly used absorbent materials are cellulosic fluff pulp, tissue layers, highly absorbent polymers (so called superabsorbents), absorbing foam material, absorbing nonwoven materials and the like. It is conventional to combined cellulosic fluff pulp and superabsorbents in an absorbent core. It is also common to have absorbent cores comrpising layers of different material or combinations of materials with regard to fluid acquisition properties, fluid spreading properties and fluid storage properties. This is wellknown in the art.

The fluid acquisition/transfer layer 8 is of the kind described above and it should have a capability to quickly acquire large amounts of body fluids discharged during a short period of time. It should further temporarily store the liquid before it is absorbed by the underlying absorbent core 9. These properties should be substantially maintained also at the second and further wettings of the material. The fluid acquisition/transfer layer 8 can either cover the entire absorbent core 9 or only the central portion thereof.

Due to the use of the resilient spiralized bicomponent fibers as functional fibers in the fluid acquisition/transfer layer 8 said layer has a big open volume for receiving liquid and it is therefore very effective in quickly acquiring large volumes of liquid. It is also effective at relatively low basis weights, e g lower than 60 g/m$^2$, which is important for cost reasons. It also quickly recovers its bulk after compression.

It is obvious that the incontinence guard described above and shown in the drawings is only one example of an absorbent article referred to by the present invention. Thus the shape and construction of the article can vary. The absorbent article may also be a diaper, a pant diaper, a sanitary napkin, a panty liner or the like.

EXAMPLE

A comparative test has been performed between a standard fluid acquisition/transport layer in the form of a carded thru-air bonded web comprising hollow functional fibers having an ordinary saw-tooth crimp and having a basis weight of 50 g/m² and a fluid acquisition/transport layer according to the invention comprising spiralized bicomponent hollow functional fibers and having the same basis weight. The same bonding fibers were used in both materials. The liquid strike-through time before and after compression of the layers were measured.

The test material according to the invention consisted of:
- 35% by weight bonding fibers, 4 dtex, bicomponent CoPET/PET fibers.
- 65% by weight functional fibers, 6 dtex, bicomponent hollow polyester/PET fibers.

The liquid strike-through time tests were performed according to EDANA standard method 150.3–96.

Before compression the liquid strike-through time for the layer containing spiralized fibers was shorther than for the standard layer, which did not contain any spiralized fibers, especially at the second and third wettings. The standard layer thus had a poorer strike-through time and retained liquid for a longer period of time as compared to the layer according to the invention.

After compression during three weeks and four hours recovery the differences were even bigger and the layer according the invention containing spiralized fibers was almost twice as effective as the standard layer.

What is claimed is:

1. A fluid acquisition/transfer layer in an absorbent article, said acquisition/transfer layer comprising:
    a mixture of heat-shrunk, spiralized, thermoplastic multicomponent functional fibers of 3.4 dtex or more, wherein components of said multicomponent functional fibers have mutually different shrinkage properties and are located in a side-by-side relationship; and
    thermoplastic bonding fibers bonded together by heat treatment, while said functional fibers are substantially unaffected by said heat treatment.

2. The fluid acquisition/transfer layer as claimed in claim 1, wherein the fluid acquisition/transfer layer comprises between 40 and 80% by weight functional fibers.

3. The fluid acquisition/transfer layer as claimed in claim 2, wherein the fluid acquisition layer comprises at least 10% by weight bonding fibers.

4. The fluid acquisition/transfer layer as claimed in claim 1, wherein the melting point of the bonding fibers is lower than the melting point for the functional fibers.

5. The fluid acquisition/transfer layer as claimed in claim 1, further comprising other types of fibers, including at least one of cellulosic fibers and crosslinked cellulosic fibers.

6. The fluid acquisition/transfer layer as claimed in claim 1, wherein the functional fibers are hollow.

7. The fluid acquisition/transfer layer as claimed in claim 1, wherein the fluid acquisition/transfer layer is made by carding and heat bonding.

8. The fluid acquisition/transfer layer as claimed in claim 7, wherein the functional fibers have a length of between 40 and 60 mm.

9. The fluid acquisition/transfer layer as claimed in claim 7, wherein the functional fibers have a length of between 20 and 70 mm.

10. The fluid acquisition/transfer layer as claimed in claim 1, wherein the fluid acquisition/transfer layer is made by airlaying or wetlaying followed by heat bonding.

11. The fluid acquisition/transfer layer as claimed in claim 10, wherein the functional fibers have a length of 20 mm or less.

12. The fluid acquisition/transfer layer as claimed in claim 1, wherein the functional fibers have thickness between of 3.4 and 50 dtex.

13. The fluid acquisition/transfer layer as claimed in claim 1, wherein the fluid acquisition/transfer layer is in the form of a laminate in which at least one of the layers comprises a mixture of functional fibers and bonding fibers.

14. The fluid acquisition/transfer layer as claimed in claim 1, wherein the fluid acquisition/transfer layer comprises between 50% and 70% by weight functional fibers.

15. The fluid acquisition/transfer layer as claimed in claim 1, wherein the fluid acquisition/transfer layer is made by carding and thru-air-bonding.

16. The fluid acquisition/transfer layer as claimed in claim 1, wherein the fluid acquisition/transfer layer is made by airlaying or wetlaying followed by thru-air-bonding.

17. The fluid acquisition/transfer layer as claimed in claim 1, wherein the functional fibers have a thickness of between 3.4 and 15 dtex.

18. The fluid acquisition/transfer layer as claimed in claim 1, wherein the fluid acquisition/transfer layer is attached to any one of a diaper, pant diaper, incontinence guard, sanitary napkin, and panty liner.

19. An absorbent article comprising:
    a liquid pervious topsheet;
    a liquid impervious backsheet;
    an absorbent core; and
    a fluid acquisition/transfer layer arranged between the topsheet and the absorbent core, wherein said fluid acquisition/transfer layer comprises:
    a mixture of heat-shrunk, spiralized, thermoplastic multicomponent functional fibers of 3.4 dtex or more, wherein components of said multicomponent functional fibers have mutually different shrinkage properties and are located in a side-by-side relationship; and
    thermoplastic bonding fibers bonded together by heat treatment, while said functional fibers are substantially unaffected by said heat treatment.

20. The absorbent article of claim 19, wherein the absorbent article is any one of a diaper, pant diaper, incontinence guard, sanitary napkin, and panty liner.

* * * * *